US009830520B2

(12) United States Patent
Maalouf et al.

(10) Patent No.: US 9,830,520 B2
(45) Date of Patent: Nov. 28, 2017

(54) METHOD FOR CHARACTERIZING MATERIAL BY ANALYSIS OF SPECKLES

(71) Applicant: Safran Identity & Security, Issy-les-Moulineaux (FR)

(72) Inventors: Aldo Maalouf, Issy les Moulineaux (FR); Florence Guillemot, Issy les Moulineaux (FR); Remy Chiu, Issy les Moulineaux (FR)

(73) Assignee: SAFRAN IDENTITY & SECURITY, Issy les Moulineaux (FR)

( * ) Notice: Subject to any disclaimer, the term of this patent is extended or adjusted under 35 U.S.C. 154(b) by 0 days.

(21) Appl. No.: 15/257,810

(22) Filed: Sep. 6, 2016

(65) Prior Publication Data
US 2017/0068865 A1  Mar. 9, 2017

(30) Foreign Application Priority Data
Sep. 7, 2015 (FR) ...................................... 15 58272

(51) Int. Cl.
*G06K 9/00* (2006.01)
*G06K 9/52* (2006.01)
(Continued)

(52) U.S. Cl.
CPC ..... *G06K 9/00906* (2013.01); *G06K 9/00899* (2013.01); *G06K 9/4604* (2013.01);
(Continued)

(58) Field of Classification Search
CPC ........... G06K 9/522; G01N 2015/0216; G01N 2021/479; G01N 21/4795; G01N 21/25; G01N 21/47
See application file for complete search history.

(56) References Cited

U.S. PATENT DOCUMENTS

2014/0055775 A1*  2/2014  Imai ......................... G01J 3/32
356/73

FOREIGN PATENT DOCUMENTS

FR         3007170 A1    12/2014
WO   WO 2006049396 A1    5/2006
(Continued)

OTHER PUBLICATIONS

Chang et al. "Fingerprint Spoof Detection Using Near Infrared Optical Analysis." State of the Art in Biometrics, INTECH, Jul. 27, 2011. pp. 57-85.
(Continued)

*Primary Examiner* — Kenny Cese
(74) *Attorney, Agent, or Firm* — Blakely Sokoloff Taylor & Zafman LLP (57) ABSTRACT

A method for characterizing material in which a surface is formed, by analysis of speckles generated on the surface by a coherent light beam by performing the computation of an autocorrelation function of the light intensity on the image and computation of the value of at least one criterion set up from said function, setting up an autocorrelation matrix of the light intensity of the image, computation of the discrete cosine transform of said matrix, and computation of the value of a characterization criterion such as the average on the image of the matrix trace obtained by the discrete cosine transform of the autocorrelation matrix, and computation of the value of at least one representative criterion of a phase shift distribution of the light beams diffused by the surface, said computation comprising computation of a wavelet transform of the image, and computation of the value of at least one criterion from the following group: average of the phases of the wavelet coefficients on the image, or standard deviation of the phases of the wavelet coefficients on the image.

9 Claims, 5 Drawing Sheets

(51) Int. Cl.
G06K 9/46 (2006.01)
G01N 21/47 (2006.01)
G01N 21/25 (2006.01)

(52) U.S. Cl.
CPC ............ *G06K 9/522* (2013.01); *G01N 21/25* (2013.01); *G01N 21/47* (2013.01); *G01N 2021/479* (2013.01)

(56) References Cited

FOREIGN PATENT DOCUMENTS

WO  WO 2006085252 A2  8/2006
WO  WO 2014198847 A1  12/2014

OTHER PUBLICATIONS

Li et al. "Autocorrelation and DCT Based Quality Metrics for Fingerprint Samples Generated by Smartphones." 18th International Conference on Digital Signal Processing, IEEE, Jul. 1, 2013. 5 pages.
Search Report in French Application No. 1558272 dated May 23, 2016, with English translation coversheet. 3 pages.

* cited by examiner

METHOD FOR CHARACTERIZING MATERIAL BY ANALYSIS OF SPECKLES

FIELD OF THE INVENTION

The invention relates to a method for characterizing material in which a surface is formed, by analysis of speckles generated on the surface by a coherent light beam.

PRIOR ART

Analysis of speckles generated on the surface of material by a coherent light beam is already being used to study properties of material.

Patent application FR3007170 discloses a method for determination of the living character or not of a tissue.

This method comprises exposure of the surface to a coherent light beam to generate speckles on said surface. Speckles are interference figures resulting from interferences of the beam diffused over the surface. An image of the speckles is acquired, then this image is analyzed to determine whether the material constituting the surface is living or not.

This method has already provided substantial service. But analysis performed on the speckle image is not sufficiently precise to determine which material this is.

Document WO2006/085252 also discloses a method for analysis of speckles generated on a surface, but this time to monitor the time evolution of the aspect of the speckles to detect the existence of underlying blood flow, and even to decide if the tissue is living or not.

Neither does this method characterize the material forming the surface.

Document WO 2006/049396 discloses a method for analysis of speckles for determining if the material constituting the surface on which the speckles appear is authentic biological tissue or a reproduction. This method is based on analysis of nuances of grey in a speckle image formed on the surface.

This method differentiates a biological tissue from a biological tissue only and therefore does not differentiate many materials, especially non-biological materials.

PRESENTATION OF THE INVENTION

The aim of the invention is to determine a material constituting a surface via analysis of speckles generated on said surface.

In this respect, the aim of the invention is a method for characterizing material in which a surface is formed, comprising the steps of:
- projecting a coherent light beam onto the surface to generate on said surface speckles resulting from interferences of the light beams diffused by said surface,
- acquiring an image of said surface on which the speckles appear,
- processing said image to compute at least one characterization criterion of the material, and
- from the criteria, determine the material constituting the surface, in which the processing step of the image comprises:
- computation of an autocorrelation function of the light intensity on the image and computation of the value of at least one criterion set up from said function, said computation comprising:
  - setting up an autocorrelation matrix of the light intensity of the image,
  - computation of the discrete cosine transform of said matrix, and
  - computation of the value of a characterization criterion as the average on the image of the matrix trace obtained by the discrete cosine transform of the autocorrelation matrix, and
- computation of the value of at least one representative criterion of a phase shift distribution of the light beams diffused by the surface, said computation comprising computation of a wavelet transform of the image, and computation of the value of at least one criterion from the following group:
  - average of the phases of the wavelet coefficients on the image, or
  - standard deviation of the phases of the wavelet coefficients on the image.

Advantageously, but optionally, the method for characterizing material according to the invention can further comprise at least one of the following characteristics:
- computation of the value of at least one characterization criterion from the autocorrelation function of the light intensity can comprise:
  - computation of the value of at least one criterion set up from the Fourier transform of the autocorrelation function, and
  - computation of the value of at least one criterion set up from the discrete cosine transform of the autocorrelation function.
- a criterion set up from the Fourier transform of the autocorrelation function can comprise at least one from the following group:
  - average of the Fourier transform of the autocorrelation function on the image, or
  - standard deviation of the Fourier transform of the autocorrelation function on the image.
- processing of the image can also comprise setting up an autocorrelation matrix of the light intensity of the image, and computation of the value of a characterization criterion equal to the square root of the sum of average eigenvalues of said matrix on the image.
- step of determining the material constituting the surface can further comprise computation of an overall score from the values of the criteria, and classification of the material by comparison of the overall score with a plurality of predetermined ranges corresponding to respective materials.

The method can also comprise a preliminary step of preparing ranges of scores, said step comprising:
- for a plurality of surfaces formed in determined materials, conducting steps of:
  - projecting onto the surface a coherent light beam to generate on said surface speckles resulting from interferences of the light beams diffused by said surface,
  - acquiring an image of said surface on which the speckles appear,
  - processing said image to compute at least one characterization criterion of the material, said processing comprising computation of an autocorrelation function of the light intensity on the image and computation of the value of at least one criterion from said function, computation of the value of at least one representative criterion of a phase shift distribution of the light beams diffused by the surface, and setting up an overall score from said values, implementing a learning mechanism on all the overall scores and all the corresponding materials to obtain the ranges corresponding to each material.

Another aim of the invention is a biometric control method comprising executing the method of the description which precedes on a surface presented by an individual during biometric control, the method further comprising emission of an alert in the event where the characterized material does not correspond to biological tissue.

The invention also relates to a characterization system of material comprising:
  a coherent source of light,
  an image sensor, and
  a processing unit, comprising a processor adapted to:
    process an image of a surface on which speckles appear, said processing comprising computation of an autocorrelation function of the light intensity on the image,
    computing, from said images, the value of at least one characterization criterion of the material forming the surface, comprising at least one criterion computed from the autocorrelation function, said computation comprising:
      setting up an autocorrelation matrix of the light intensity of the image,
      computation of the discrete cosine transform of said matrix, and
      computation of the value of a characterization criterion as the average on the image of the matrix trace obtained by the discrete cosine transform of the autocorrelation matrix, and at least one representative criterion of a phase shift distribution of the light beams diffused by the surface, computation of this criterion comprising computation of a wavelet transform of the image, and computation of the value of at least one criterion from the following group:
        average of the phases of the wavelet coefficients on the image, or
        standard deviation of the phases of the wavelet coefficients on the image, and
    from the values of the criteria, determine the material constituting the surface.

The final aim of the invention is a computer program product, comprising code instructions for executing a method comprising processing an image of a surface to compute the value of at least one characterization criterion of the material constituting the surface, said processing comprising:
  computation of an autocorrelation function of the light intensity on the image and the computation of the value of at least one criterion set up from said function, comprising:
    setting up an autocorrelation matrix of the light intensity of the image,
    computation of the discrete cosine transform of said matrix, and
    computation of the value of a characterization criterion as the average on the image of the matrix trace obtained by the discrete cosine transform of the autocorrelation matrix, and
  computation of the value of at least one representative criterion of a phase shift distribution of the light beams diffused by the surface, comprising computation of a wavelet transform of the image, and computation of the value of at least one criterion from the following group:
    average of the phases of the wavelet coefficients on the image, or
    standard deviation of the phases of the wavelet coefficients on the image,
  when executed by a processor.

The proposed invention characterizes the material forming a surface by analysis of speckles generated on the surface by a coherent light beam. In fact, different materials generate speckles having different properties.

The use of at least one criterion based on the autocorrelation of the light intensity and of at least one criterion based on the phase shifts of the light beams diffused by the surface analyses different characteristics of materials and discriminates between a high number of materials.

In fact, autocorrelation of the light intensity translates a more or less highly diffusive character of the material (for discriminating for example between silicone and paper or plaster). The phase shift distribution characterizes as such the relief of the surface since phase shift varies as a function of the height of the point of the surface on which the beam has been diffused. It therefore characterizes materials according to the criterion of the relief (for discriminating for example between paper and porcelain).

Also, the criteria based on autocorrelation of the light intensity of the image can in turn reflect different characteristics of the speckles of the image and can also improve precision of the characterization of the method. For example, criteria set up from the spectral density of power describe the distribution of the sizes of the speckle patterns, whereas other criteria can describe a distribution of intensity of the speckle patterns.

DESCRIPTION OF THE FIGURES

Other characteristics, aims and advantages of the present invention will emerge from the following detailed description, with respect to the appended figures, given by way of non-limiting examples and in which.

DETAILED DESCRIPTION OF AT LEAST ONE EMBODIMENT OF THE INVENTION

Figure 1A:
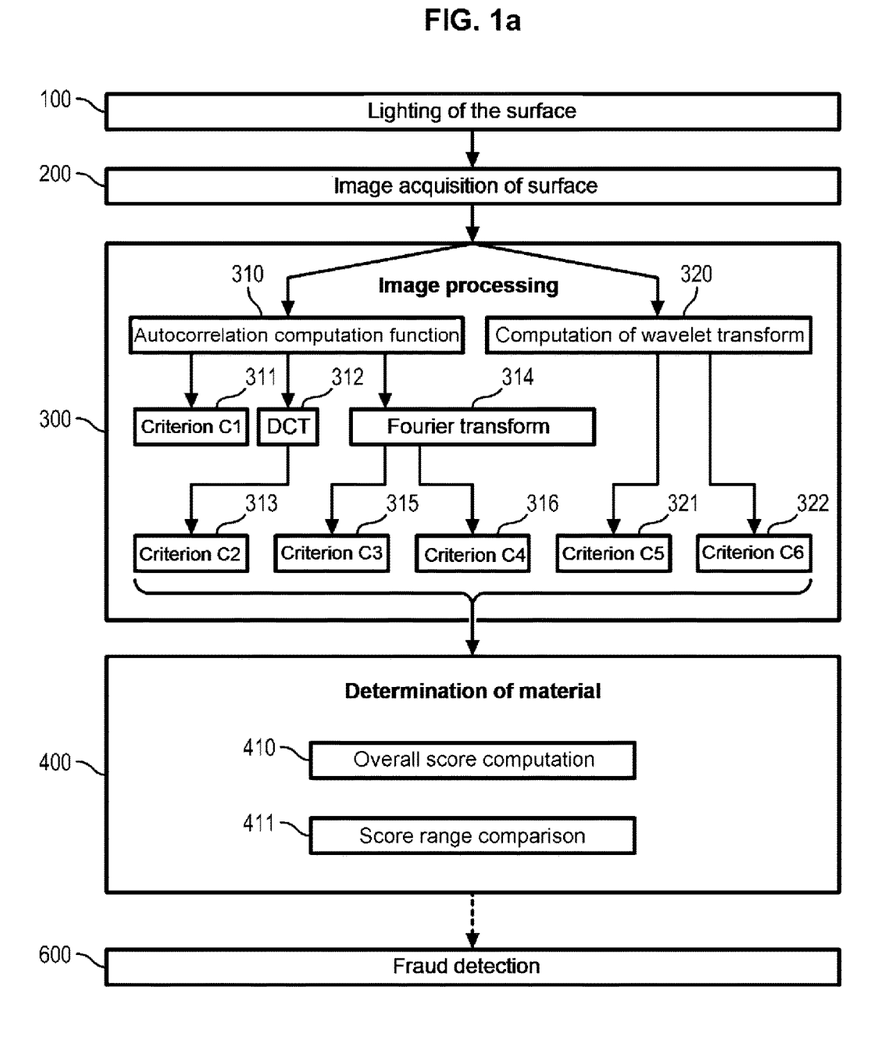
FIG. 1a schematically illustrates the main steps of a method for characterizing material according to an embodiment of the invention.

In reference to FIG. 1, this schematically illustrates the main steps of a method for characterizing material constituting a surface S. This method can be executed during a biometric control, during which an image of a biometric trait formed on the surface is acquired. Typically, a biometric trait can be a fingerprint or the shape of the face.

The aim of the method is to determine the material in which the surface is formed, for example if it is formed from biological tissue, typically epidermis, or a material such as paper or silicone, which can be used for fraud.

The method comprises a first step 100 of lighting the surface with a coherent light beam, i.e., the light beams of which present a coherence length advantageously greater than 1 cm, to generate speckles on this surface.

The method further comprises a second step 200, performed simultaneously with the first, of acquisition of at least one image of the surface S showing the speckles, such that the speckles appear on the image.

Figure 2:
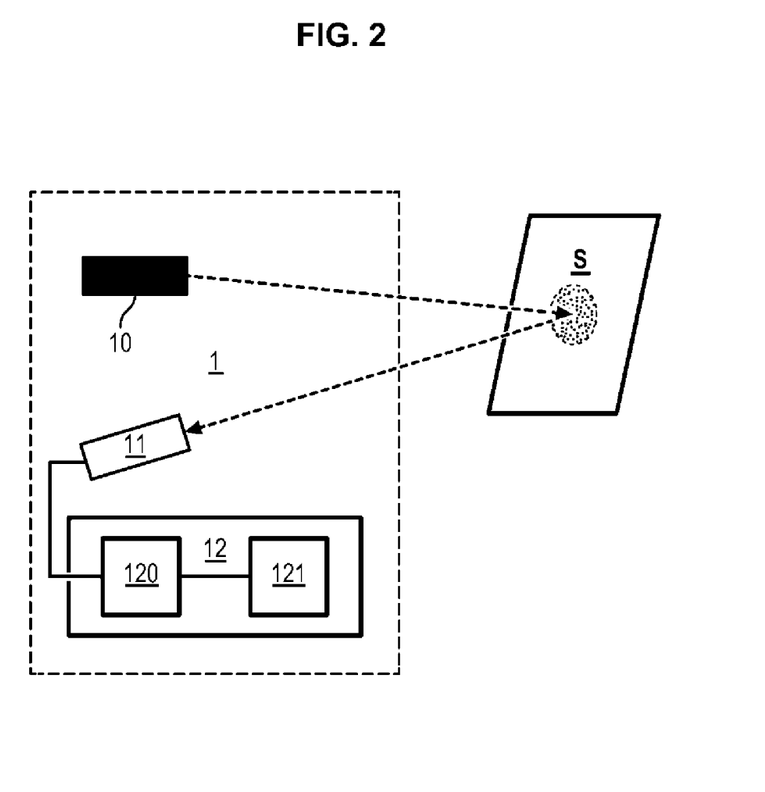

FIG. 2 shows a system 1 adapted for executing the method for characterizing the material. To perform the lighting step 100, this system comprises a coherent light source 10.

This source is advantageously a laser or a monomode laser diode. Light sources have a coherence length of the order of a few tens of micrometers, such that LED, or of the order of a few micrometers, such as white light, are proscribed.

The light source 10 comprises advantageously a polarizer adapted so that the emitted light beam has rectilinear polarization.

The lighting of the surface S by the light beam reveals speckles on this surface.

For conducting step 200 of acquisition of image(s), the system 1 advantageously comprises an image sensor 11 sensitive to the same wavelength as the light emitted by the source 10, and comprising a polarizer (not shown) parallel or perpendicular to the direction of polarization of the light beam emitted by the source 10.

The image sensor can for example be a digital camera or a digital photographic unit.

The system 1 preferably further comprises a processing unit 12 typically comprising at least one processor 120, and a memory 121, to execute processing 300 of the image described hereinbelow.

Figure 3:
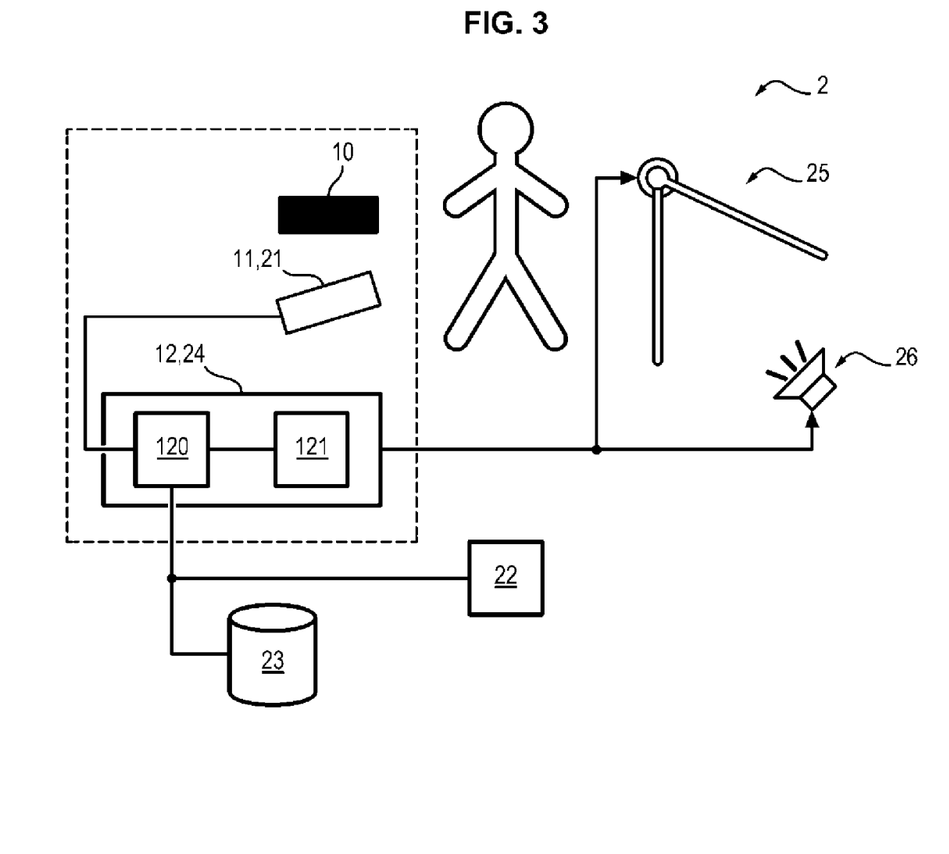
FIG. 3 schematically illustrates a system for identifying or authenticating an individual.

In reference to FIG. 3, when the method for characterizing material is executed during a biometric control, the system 1 is advantageously integrated into an identification or authentication system 2.

This system 2 comprises a biometric sensor 21, which can be separate or combined with the image sensor 11. For example, when the analyzed biometric trait is a fingerprint, the image sensor 11 can be used both to acquire an image of the print and to acquire a speckle image generated on the finger where the print is located.

The identification or authentication system can further comprise a reader 22 adapted to obtain, by reading an optionally digital identity document, a reference biometric datum. For example, the biometric datum can be registered in a chip kept in the identity document. The reader 22 is in this case adapted to access the content stored in the chip. Alternatively, in the case for example where the biometric trait analyzed is the shape of the face, a photograph of the individual can feature in the identity document and the reader 22 can be an image sensor adapted to acquire an image of this photograph.

Alternatively, the identification or authentication system can comprise a database 23 storing all reference biometric data.

This system further comprises a processing unit 24, comprising a processor adapted to compare the biometric datum acquired on the individual to a reference datum obtained from an identity document or a datum registered in the database. Advantageously the processing unit 24 is combined with the unit 12, i.e., the same unit performs authentication or identification and detection of fraud by characterization of the material forming the surface of the analyzed biometric trait.

In the event where identification or authentication is implemented to control physical access of the individual to a zone, the system can comprise an access restriction device 25 which can be controlled by the processing unit to block or authorize access of the individual to the zone. The device 25 is typically a barrier, a door which can be locked or unlocked, etc.

The system finally comprises an alarm 26 which can be activated by the processing unit 24 in case of detection of fraud. The alarm 26 can be for example a sound signal or a visual signal such as illumination of a light or the display, on a screen, of an alert message.

Again, FIG. 1, once an image is acquired of the speckles made on the surface, the method for characterizing material comprises a processing step 300 of the acquired image(s) to compute values of statistical characterization criteria of the material constituting the surface. This step is advantageously performed by the processing unit 12 of the system 1.

Criteria Based on the Autocorrelation Function

The processing step 300 is described hereinbelow for an image. In the event where several images of the surface are acquired at step 200, the images can be processed identically and the values computed during processing 300 are in this case advantageously averaged over all the images processed.

Processing an image comprises computation 310 of the spatial autocorrelation function of the light intensity on the image. This function is a statistical parameter which provides an indication on the size of grains in the speckles and on their distribution. The autocorrelation function is expressed as follows:

$$\rho(l, m) = \frac{\langle (I(x, y) - \langle I \rangle)I(x + l, y + m) - \langle I \rangle) \rangle}{\sigma^2}$$

where $\sigma$ is the standard deviation of the light intensity in the image, $\langle I \rangle$ is the average value in the image of the light intensity I, (x,y) defines the position of a pixel in the image, and l and m translate a distance in the directions of x and y.

Different statistical criteria can be used from the autocorrelation function.

Advantageously, the statistical criteria are computed solely on the pixels of the image corresponding to a speckle figure. The surface s covered by the speckles, which is defined as the double integral of the autocorrelation function, is preferably computed to identify these pixels:

$$s = \int_{-\infty}^{+\infty} \int_{-\infty}^{+\infty} \rho(l, m) \, dl \, dm$$

A first material characterization criterion can be defined from a so-called autocorrelation matrix A. This matrix A is obtained by reformulating the autocorrelation function as follows, for small offsets l and m:

$$\rho(l, m) = \sum_{(x,y) \in w} [I(x, y) - I(x + \Delta x, y + \Delta y)]^2$$

Where w is a window of pixels of the image, for example a window of three pixels per side.

Applying the Taylor expansion to I (x+Δx, y+Δy) gives:

$$I(x+\Delta x, y+\Delta y) = I(x, y) + \frac{\partial I}{\partial x}\Delta x + \frac{\partial I}{\partial y}\Delta y$$

Setting up $$I_x = \frac{\partial I}{\partial x} \text{ and } I_y = \frac{\partial I}{\partial y},$$

gives:

$$I(x+\Delta x, y+\Delta y) = I(x, y) + I_x \Delta x + I_y \Delta y$$

And making the variable change X=(x y) gives:

$$I(x, y)I_x\Delta x + I_y\Delta y = I(X) + (\nabla I)\Delta X$$

Where $\nabla I = (I_x, I_y)^T$
Giving:

$$\rho(l, m) = \sum_w [I_x\Delta x + I_y\Delta y]^2 = \sum_w [I_x^2 \Delta x + 2I_x I_y \Delta x \Delta y + I_y^2 \Delta^2 y] = (\Delta X)^T A(X)(\Delta X)$$

With the autocorrelation matrix A defined at any point (x,y) of the image by:

$$A = \begin{bmatrix} \sum_w I_x^2 & \sum_w I_x I_y \\ \sum_w I_x I_y & \sum_w I_y^2 \end{bmatrix}$$

The eigenvalues noted λ+ and λ− of this matrix indicate the degree of autocorrelation of a pixel (x,y) relative to the adjacent pixels. The values of λ+ and λ− on the image therefore produce distribution of intensity in the field w, which is not the same for different types of materials. In particular, a biological tissue presents a stronger autocorrelation than material used for a fraud.

Consequently a first characterization criterion $C_1$ can be defined from the eigenvalues of the matrix A. Advantageously, this criterion is defined as:

$$C_1 = \sqrt{\Lambda_+ + \Lambda_-}$$

Where $\Lambda_+$ is the average of the eigenvalues λ+ on the image, and $\Lambda_-$ is the average of the eigenvalues λ− on the image.

So the method advantageously comprises a computation step 311 of the value of the criterion $C_1$ for the image acquired at the step 200.

Alternatively, or cumulatively with the value of the first characterization criterion $C_1$, the value of a second criterion $C_2$ can be computed from the matrix A.

To compute the value of this second criterion, the method comprises an additional computation step 312 of the discrete cosine transform (DCT) of the autocorrelation matrix A.

This step modifies the matrix A in a Toeplitz matrix A', i.e., a matrix whereof the coefficients located on each diagonal are the same. In this case the matrix A' therefore has the shape:

$$\begin{bmatrix} a & b \\ c & a \end{bmatrix}$$

Due to this, the eigenvalues of the matrix A' correspond to the power minimum and maximum of the spectrum of the intensity I on the pixel (x,y); the eigenvalues of A' are maximum when autocorrelation in the image is strong.

The second criterion $C_2$ can therefore be defined from the matrix trace A', which is an approximation of the sum of the eigenvalues of A'. This criterion can for example be the average on the image of the trace of A'. The higher this average, the higher the autocorrelation in the image.

So the method advantageously comprises the computation 313 of the value of the criterion $C_2$ from the image acquired at step 200.

Alternatively or cumulatively to the preceding criteria, a characterization criterion set up from the autocorrelation function can be provided by the Fourier transform of the autocorrelation function. In this case, the processing step 300 comprises a computation step 314 of the Fourier transform of the autocorrelation function of the light intensity, noted F(ρ(l,m)).

According to the Weiner-Khinchin theorem, the Fourier transform of the autocorrelation function is equal to the power spectral density of the intensity:

$$F(\rho(l,m)) = PSD(I)$$

The power spectral density describes the distribution of sizes of patches in the figure formed by the speckles. It is therefore exploited to characterize materials.

A third correlation criterion $C_3$ is defined as the standard deviation of the power spectral density of the intensity on the image, which is computed as the standard deviation of the Fourier transform of the autocorrelation function on the image.

A fourth correlation criterion $C_4$ is defined as the average of the power spectral density of the intensity on the image, which is computed as the average of the Fourier transform of the autocorrelation function on the image.

The method advantageously comprises a computation step of the value of at least one criterion set up from the Fourier transform, either the criterion $C_3$ (step 315), or the criterion $C_4$ (step 316).

The criterion or the criteria described hereinabove set up from the autocorrelation function are advantageously combined into at least one additional criterion representative of the phase shift distribution of the light beams diffused by the surface.

In other words, the method comprises computation of the value of at least one of the criteria described hereinabove, and of the value of at least one criterion defined hereinbelow relative to phase shift of the light beams.

Criteria of a Phase Shift Distribution

The processing step 300 of the image comprises a step 320 of the wavelet transform of the image to characterize the phase shifts of the light beams diffused by the surface.

In fact, surface defects cause phase shifts on the light beams, which are a function of the heights of the defects. The field U at a given point P can therefore be expressed as a discrete sum of the contributions of the light beams coming from a set of N defects, the light beams coming from the same defect having all the same phase shift $\phi_n$:

$$U(P) = \sum_{n=1}^{N} a_n e^{i\varphi_n}$$

Where $a_n$ designates the amplitude of the field of the light beams diffused by the defect n.

When the number of defects N is considerable, the central limit theorem applies to the preceding equation, and the field at a point of observation U(P) follows a Gaussian law; the speckles are qualified as Gaussian.

The wavelet transform 320 of the image estimates the values of the field $a_n$ and of the phase shift $\phi_n$ by selecting a scale e adapted so that the number of defects N considered in the image is sufficiently large for the field to follow a Gaussian law.

To model the Gaussian field, by adapting the works of Mallat et al. in the publication *Characterization of signals from multiscale edges, IEEE Transaction on Pattern Analysis* and *Machine Intelligence*, 14: 710-732, 1992, a Gaussian function $\theta(x_{,y})$, and two wavelet functions $\psi^1$ and $\psi^2$ are defined as being respectively the derivatives at x and y of the function $\theta$:

$$\psi^1(x, y) = \frac{\partial \theta(x, y)}{\partial x}$$

$$\psi^2(x, y) = \frac{\partial \theta(x, y)}{\partial y}$$

For an image having a light intensity $I(x, y) \in L^2(\mathbb{R}^2)$, the wavelet transform on the scale e of the light intensity I of the image has two components:

$$D_e^1 = I * \psi_e^1(x, y) = I * \left( e \frac{\partial \theta_e(x, y)}{\partial x} \right) = e \frac{\partial (\theta_e * I)(x, y)}{\partial x}$$

$$D_e^2 = I * \psi_e^2(x, y) = I * \left( e \frac{\partial \theta_e(x, y)}{\partial y} \right) = e \frac{\partial (\theta_e * I)(x, y)}{\partial y}$$

So on a scale e, the amplitude of fields at (x,y) is defined by:

$$a = \sqrt{(D_e^1)^2 + (D_e^2)^2}$$

And the phase is defined by:

$$\varphi = \tan^{-1}\left( \frac{D_e^2}{D_e^1} \right)$$

A fifth correlation criterion $C_5$ is then defined as the standard deviation of the phases of the wavelet coefficients on the image.

A sixth correlation criterion $C_6$ is finally defined as the average of the phases of the wavelet coefficients on the image.

The method therefore advantageously comprises computation of the value of at least one of the criteria $C_5$ (step 321), $C_6$ (step 322), or the two criteria.

So during a step 400, the processor determines the nature of the material from the values of the criteria computed at the preceding step, and especially from at least one of the four criteria obtained from the autocorrelation function of the light intensity, and of at least one of the two presented criteria obtained from the wavelet transform of the light intensity of the image.

For greater precision in the characterization of the material, the values of all the criteria described hereinabove are preferably computed and considered in step 400.

The characterization step 400 of the material first comprises aggregation 410 by the processor 120 of the values of the criteria obtained for forming an overall score. The overall score can for example be a vector comprising all the values of the criteria. Alternatively, the overall score can be a linear combination of the values of the criteria or, more preferably, a polynomial evaluated in these values.

Next, the processor 120 compares 411 the overall score obtained to all the predetermined ranges corresponding to respective materials. According to the range containing the overall score for the analyzed image, the corresponding material can be identified.

Figure 1B:
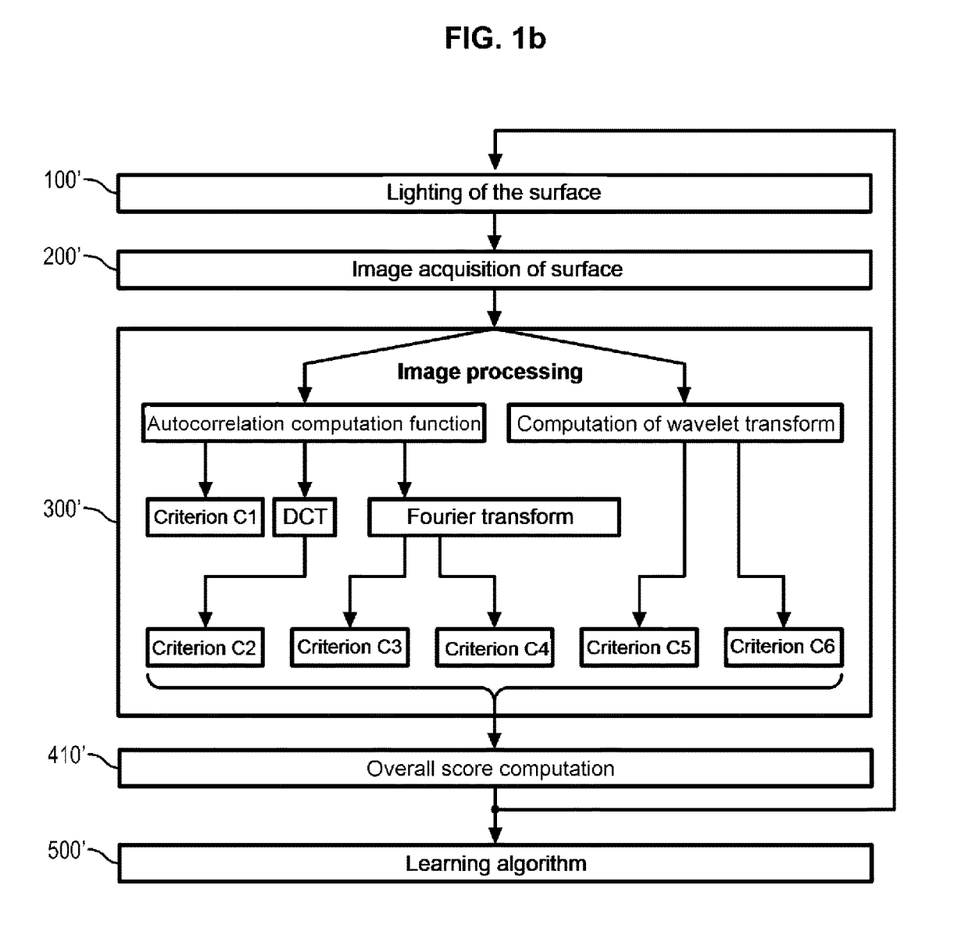
FIG. 1b schematically illustrates the main steps of preparing ranges of values of overall score to characterize a material, FIG. 2 schematically illustrates a system for executing the method for characterizing material.

The ranges of scores corresponding to materials are preferably prepared prior to a step 500 shown in FIG. 1*b*. For this, steps similar to those described hereinabove of lighting 100', acquisition of a speckle image 200', processing of the image 300', and computation of an overall score 410', are performed over a large number of surfaces, each surface being formed from a determined material. For example, surfaces made of materials such as the epidermis, skin, beeswax, glue, gelatin, latex, plasticine, porcelain, silicone, etc., are analyzed with a view to setting up corresponding ranges of scores.

The scores obtained for each surface are then aggregated during step 500 by a learning algorithm, for example of SVM (Support Vector Machine) type, analysis in main components, or others, to produce the ranges of scores corresponding to each material.

Advantageously, the learning algorithm prepares a polynomial for best separating the test materials. In this way, later evaluation of the same polynomial from the values of the criteria computed for a candidate material determines the nature of the candidate material with certainty.

Figure 4:
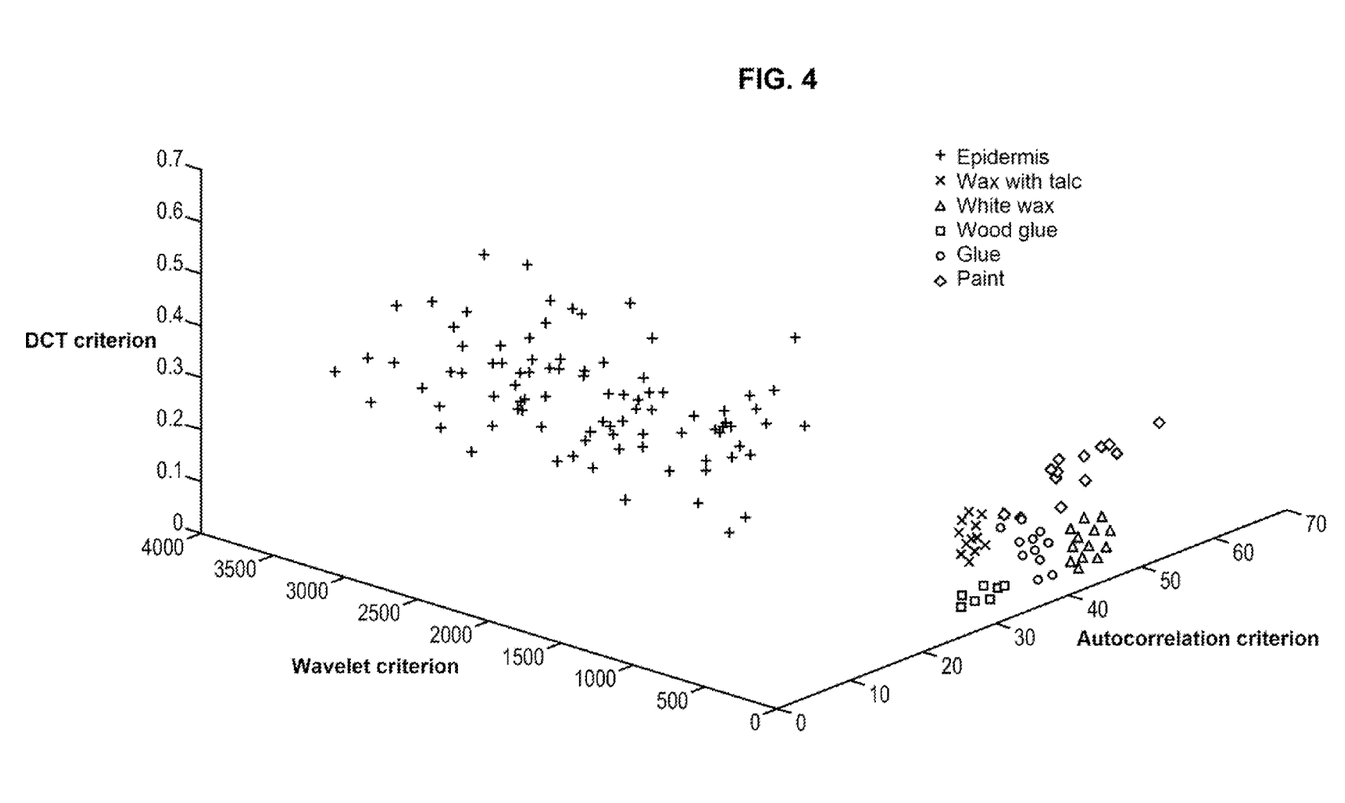
FIG. 4 illustrates an example of results obtained by using two criteria based on the autocorrelation function, one of which is obtained from the discrete cosine transform of said function, and a representative criterion of the phase shift distribution.

In reference to FIG. 4, this shows examples of overall scores represented for a set of materials, the scores being set from a criterion computed from the wavelet transform, a criterion computed from the discrete cosine transform of the autocorrelation function, and the criterion $C_1$. It is evident that the cumulated use of several criteria including a criterion computed from the wavelet transform not only distinguishes the epidermis from fraudulent materials, but also distinguishes fraudulent materials from each other.

Back to FIG. 1, when the method described hereinabove is carried out within the scope of a biometric control, it advantageously comprises a step 600 for detection of fraud and emission of an alert, in the event where the material identified is not a biological tissue, especially not epidermis.

This implies that the processing unit 24 controls activation of the alarm 26, for example by emission of a visual signal (light signal, display of an alert message) or sound signal, and initiates locking (or maintaining in the closed state) of the access restriction device 25.

If on the contrary the material is identified as a biological tissue forming the biometric trait on which identification or authentication is based, the method can conventionally continue as an identification or authentication method performed by the system 2 by comparison of a biometric datum acquired on the individual with a reference datum.

The invention claimed is:

1. A method for characterizing material in which a surface is formed, comprising the steps of:
    projecting a coherent light beam onto the surface to generate on said surface speckles resulting from interferences of the light beams diffused by said surface, acquiring an image of said surface on which the speckles appear, processing said image to compute at least one characterization criterion of the material, and from criteria, determining the material constituting the surface, in which the processing step of the image comprises:

computation of an autocorrelation function of the light intensity on the image and computation of the value of at least one criterion set up from said function, said computation comprising:

setting up an autocorrelation matrix of the light intensity of the image, computation of the discrete cosine transform of said matrix, and computation of the value of a characterization criterion such as the average on the image of the matrix trace obtained by the discrete cosine transform of the autocorrelation matrix, and computation of the value of at least one representative criterion of a phase shift distribution of the light beams diffused by the surface, said computation comprising computation of a wavelet transform of the image, and computation of the value of at least one criterion from the following group:

average of the phases of the wavelet coefficients on the image, or standard deviation of the phases of the wavelet coefficients on the image.

2. The characterization method according to claim 1, wherein computation of the value of at least one characterization criterion from the autocorrelation function of the light intensity comprises:

computation of the value of at least one criterion set up from the Fourier transform of the autocorrelation function, and computation of the value of at least one criterion set up from the discrete cosine transform of the autocorrelation function.

3. The characterization method according to claim 2, wherein the criterion set up from the Fourier transform of the autocorrelation function comprises at least one from the following group:

average of the Fourier transform of the autocorrelation function on the image, or standard deviation of the Fourier transform of the autocorrelation function on the image.

4. The characterization method according to claim 1, wherein processing of the image comprises setting up an autocorrelation matrix of the light intensity of the image, and computation of the value of a characterization criterion equal to the square root of the sum of the average eigenvalues of said matrix on the image.

5. The characterization method according to claim 1, wherein the determination step of the material constituting the surface comprises computation of an overall score from the values of the criteria, and classification of the material by comparison of the overall score with a plurality of predetermined ranges corresponding to respective materials.

6. The characterization method according to claim 5, further comprising a preliminary step of preparing ranges of scores, said step comprising:

for a plurality of surfaces formed in determined materials, performing steps of:

projecting onto the surface a coherent light beam to generate on said surface speckles resulting from interferences of the light beams diffused by said surface, acquiring an image of said surface on which the speckles appear, processing said image to compute at least one characterization criterion of the material, said processing comprising computation of an autocorrelation function of the light intensity on the image and computation of the value of at least one criterion from said function, computation of the value of at least one representative criterion of a phase shift distribution of the light beams diffused by the surface, and setting up an overall score from said values, implementing a learning mechanism on all the overall scores and all the corresponding materials to obtain the ranges corresponding to each material.

7. A biometric control method, comprising executing the method according to claim 1 on a surface presented by an individual during biometric control, the method further comprising emission of an alert in the event where the characterized material does not correspond to biological tissue.

8. A system for characterizing a material comprising:

a coherent light source, an image sensor, and a processing unit, comprising a processor adapted to:

process an image of a surface on which speckles appear, said processing comprising computation of an autocorrelation function of the light intensity on the image, computing, from said images, the value of at least one characterization criterion of the material forming the surface, comprising at least one criterion computed from the autocorrelation function, said computation comprising:

setting up an autocorrelation matrix of the light intensity of the image, computation of the discrete cosine transform of said matrix, and computation of the value of a characterization criterion such as the average on the image of the matrix trace obtained by the discrete cosine transform of the autocorrelation matrix, and at least one representative criterion of a phase shift distribution of the light beams diffused by the surface, computation of said criterion comprising computation of a wavelet transform of the image, and computation of the value of at least one criterion from the following group:

average of the phases of the wavelet coefficients on the image, or standard deviation of the phases of the wavelet coefficients on the image, and from values of criteria, determining the material constituting the surface.

9. A non-transitory computer readable medium of a processor comprising the processing of an image of a surface to compute the value of at least one characterization criterion of the material constituting the surface, said processing comprising:

computation of an autocorrelation function of the light intensity on the image and computation of the value of at least one criterion set up from said function, said computation comprising:

setting up an autocorrelation matrix of the light intensity of the image, computation of the discrete cosine transform of said matrix, and computation of the value of a characterization criterion such as the average on the image of the matrix trace obtained by the discrete cosine transform of the auto-correlation matrix, and computation of the value of at least one representative criterion of a phase shift distribution of the light beams diffused by the surface, comprising computation a wavelet transform of the image, and computation of the value of at least one criterion from the following group:

average of the phases of the wavelet coefficients on the image, or standard deviation of the phases of the wavelet coefficients on the image, when executed by a processor.

* * * * *